(12) United States Patent
Ogawa et al.

(10) Patent No.: US 6,620,418 B1
(45) Date of Patent: Sep. 16, 2003

(54) ANTISEPTIC/ANTIFUNGAL AGENT AND ENDERMIC LINIMENT COMPOSITION WHICH CONTAINS IT

(75) Inventors: Shigeyuki Ogawa, Yokohama (JP); Yoshio Asaka, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 09/537,261

(22) Filed: Mar. 29, 2000

(30) Foreign Application Priority Data

| Mar. 30, 1999 | (JP) | 11-087741 |
| Mar. 30, 1999 | (JP) | 11-089072 |
| Jan. 18, 2000 | (JP) | 2000-008746 |

(51) Int. Cl.⁷ .................. A61K 6/00; A61K 31/045; A61K 7/00; A61K 31/075; A61K 31/08; A01N 25/00; A01N 31/14; A01N 31/00
(52) U.S. Cl. .................. 424/401; 424/405; 514/715; 514/718; 514/723; 514/724; 514/730; 514/738
(58) Field of Search .................. 424/401, 78.08, 424/405; 514/715, 717, 723, 724, 730, 738, 718

(56) References Cited

U.S. PATENT DOCUMENTS

| 2,413,803 A | | 1/1947 | Tribit | |
| 4,057,648 A | * | 11/1977 | Hool et al. | 514/721 |
| 4,868,217 A | * | 9/1989 | Araki et al. | 514/642 |
| 5,180,585 A | * | 1/1993 | Jacobson et al. | 424/405 |
| 5,494,533 A | * | 2/1996 | Woodin et al. | 134/40 |
| 5,503,840 A | * | 4/1996 | Jacobson et al. | 424/421 |
| 5,696,169 A | * | 12/1997 | Otsu et al. | 514/675 |
| 5,744,150 A | * | 4/1998 | Cercone | 424/404 |
| 6,013,275 A | * | 1/2000 | Konagaya et al. | 424/443 |
| 6,153,204 A | * | 11/2000 | Fanger et al. | 424/401 |

FOREIGN PATENT DOCUMENTS

| JP | 07316002 | * | 12/1995 |
| JP | 10081606 | * | 3/1998 |

OTHER PUBLICATIONS

"Aldrich—Chimie fine—Reactifs de Laboratoire" 1994, Sigma–Aldrich Chimie S.A.R.L. XP002137465.
"Aldrich–Chimie fine–Reactifs de Laboratoire", 1994, 273, 523, 705, 1025 and 1064.

* cited by examiner

*Primary Examiner*—Sreeni Padmanabhan
*Assistant Examiner*—Lauren Q. Wells
(74) *Attorney, Agent, or Firm*—Townsend & Banta

(57) ABSTRACT

An antiseptic/antifungal agent comprising 2,2-dialkyl-1,3-propanediol represented by the formula (I):

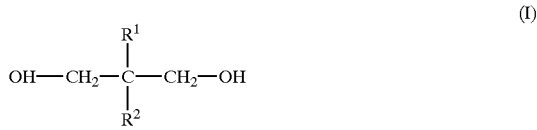

(I)

wherein $R^1$ and $R^2$ can either be identical or different from each other, and both denote an alkyl group with a carbon number of 1–4, and an endermic liniment containing the same. In addition, an endermic liniment containing 3-methyl-3-methoxybutanol and 1,2-pentanediol, and an endermic liniment containing 3-methyl-3-methoxybutanol and 2-phenoxyethanol, is provided.

5 Claims, No Drawings

ANTISEPTIC/ANTIFUNGAL AGENT AND ENDERMIC LINIMENT COMPOSITION WHICH CONTAINS IT

RELATED APPLICATION

This application claims the priority of Japanese Patent applications No. 11-087741 and No. 11-089072 filed on Mar. 30, 1999, and No. 2000-008746 filed on Jan. 18, 2000, which are incorporated herein by reference.

BACKGROUND OF THE INVENTION

1. Field of the Invention

This invention relates to a antiseptic/antifungal agent and an endermic liniment composition which contains it.

2. The Prior Art

Generally, an endermic liniment composition such as a cosmetic contains an antiseptic/antifungal agent (in the present specifications, "antiseptic" also means "antifungal" unless specified otherwise) such as paraoxy benzoate (so called parabens), salicylic acid, and sorbic acid and/or an antiseptic assistant such as phenoxy ethanol, for the purpose of improving the shelf life of the products by suppressing replication of microorganisms which contaminate the composition from outside and eventually killing off these microorganisms.

Antiseptic components such as paraben and/or antiseptic assistant components such as phenoxy ethanol have superior safety and efficacy when used as an antiseptic component in an endermic liniment composition. However, they still may cause irritation and such to a small number of very sensitive users.

Recently, endermic liniment compositions which are gentler to the skin are more in demand, and therefore the requirements of today's endermic liniment compositions are very difficult to meet by simply adding these parabens and phenoxy ethanol as the antiseptic components.

Of course it is possible to create an endermic liniment composition which does not have antiseptic components such as parabens or antiseptic assistant components such as phenoxy ethanol. However, in such a case, in order to ensure the antiseptic properties, the amount and/or the expiration date have to be limited or a complex means such as small subdivided containers or the backless mechanism has to be used, resulting in a tendency towards low economic benefits and versatility.

BRIEF SUMMARY OF THE INVENTION

Therefore, the object of the present invention is to provide a new antiseptic agent which has much superior safety and usability and can be blended into endermic liniment compositions, as well as an endermic liniment composition which contains it.

The inventors conducted earnest research to achieve the aforementioned object, and, as a result, discovered that 2,2-dialkyl-1,3-propanediol has a superior antiseptic effect and that it can be used as the effective ingredient of an antiseptic/antifungal agent. The inventors also discovered that an endermic liniment composition containing this antiseptic/antifungal agent has a superior antiseptic effect and that, even when the amount of parabens and/or phenoxy ethanol is substantially reduced, an anti septic properties adequate for normal use can be ensured. The inventors also discovered that, depending on the blend ratio of 2,2-dialkyl-1,3-propanediol, adequate antiseptic properties can be ensured in an endermic liniment composition without adding any parabens and/or phenoxy ethanol, thus completing the present invention.

That is, the present invention provides an antiseptic/antifungal agent in which 2,2-dialkyl-1,3-propanediol represented by the following general formula (I) is an effective component:

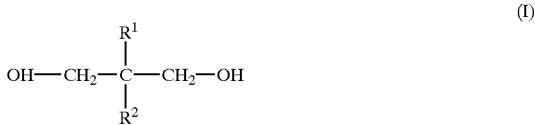

[In this formula, $R^1$ and $R^2$ can either be identical or different from each other, and both denote an alkyl group with a carbon number of 1–4.]

Also, the present invention provides an endermic liniment composition which contains the antiseptic agent of the present invention (hereafter referred to as "the endermic liniment composition of the present invention").

As mentioned above, in the endermic liniment composition of the present invention, it is possible to use 2,2-dialkyl-1,3-propanediol represented by general formula (I) as essentially the only antiseptic agent.

The inventors conducted the aforementioned research, and, as a result, discovered that, by blending a combination of 3-methyl-3-methoxybutanol, which has been widely used as a solvent for perfumes, and 2-phenoxy ethanol, which has been widely used as an antiseptic assistant, or 1,2-pentanediol, which has been widely used as a humectant, a surprisingly superior antiseptic effect is manifested and that antiseptic properties adequate for normal use can be ensured even if the blend ratios of parabens and/or phenoxy ethanol are significantly reduced. That is, although there have been examples of use of both of these compounds, they have not been used together, and the present invention discovered that the combined use of these compounds manifests a superior antiseptic effect and ensures the antiseptic properties.

The inventors discovered in particular that, depending on the blend ratios when combining 3-methyl-3-methoxybutanol and 1,2-pentanediol, adequate antiseptic properties can be ensured without using any parabens, and verified that usability and safety were excellent, thus completing the present invention. That is, the present invention provides an endermic liniment composition, such as various cosmetics, containing 3-methyl-3-methoxybutanol and 1,2-pentanediol or 2-phenoxy ethanol, which has superior antiseptic properties as well as superior usability and safety.

DETAILED DESCRIPTION OF THE INVENTION

In this invention, "an endermic liniment composition" includes all compositions used for endermic use; for example it includes compositions which can be used widely in cosmetics such as foundation cosmetics, makeup cosmetics, hair cosmetics, etc. as well as in various drugs and/or quasi drugs such as ointments. The present invention also provides these modes of endermic liniment composition individually. In the present invention, "antiseptic" means resistance against all contaminating microorganisms such as bacteria, fungi, yeast, etc., and "antiseptic effectiveness" means protection against all these contaminating microorganisms. Therefore, even when only the word "antiseptic" is used in the present specifications, the concept of "antimildew" is not excluded.

Embodiments of the present invention are described below.

"The Invention Described in Claims 1–5"

A. The Effective Component of the Antiseptic Agent of the Present Invention and Specific Embodiments 2,2-dialkyl-1, 3-propanediol which is used as an effective component of the antiseptic agent of the present invention is a neopentyl-type 1,3-propanediol represented by the above formula (I) hereafter this 2,2-dialkyl-1,3-propanediol (I) is also referred to as "compound (I)".

Different or identical alkyl groups with a carbon number of 1–4 which can be used for $R^1$ and $R^2$ include a methyl group, ethyl group, n-propyl group, isopropyl group, n-bbutyl group, isobutyl group, secondary butyl group, and tertiary butyl group.

Compound (I) is generally known as an prior art and has been disclosed in general engineering literature and/or patents in many forms. However, usually this is widely used as the raw material of urethane products and as a component of an insect repellent, and there has been no case where this was used as an effective component of an antiseptic agent.

Examples of compound (I) which are particularly superior in their antiseptic effect, less irritating, and superior in terms of usability of endermic liniments containing them include those whose $R^1$ and $R^2$ are a ethyl group, n-propyl group, isopropyl group, or n-butyl group ($R^1$ and $R^2$ can be either identical or different from each other). In particular, 2-n-butyl-2-ethyl-1,3-propanediol is easy to obtain and synthesize at the time of filing this application. Therefore, considering both the practical and economical aspects of implementation of the present invention, 2-n-butyl-2-ethyl-1,3-propanediol is superior as an effective component of the antiseptic agent of the present invention.

Compound (I) other than 2-n-butyl-2-ethyl-1,3-propanediol can also be prepared according to a prior art method, and such a product can be used for an effective component of the antiseptic agent of the present invention. Some examples of compound (I), including 2-n-butyl-2-ethyl-1,3-propanediol, are commercially available (products from Kyowa Hakko K.K., for example), and these commercial products can also be used as an effective component of the antiseptic agent of the present invention.

Compound (I) can either be used as it is for the antiseptic agent of the present invention or diluted/extended by using a diluent, filler or such.

As discussed later, compound (I) is preferably used in combination with propylene glycol and/or diols in an endermic liniment composition, and therefore both compound (I) and propylene glycol and/or diols (specific details will be given below) can be added to the antiseptic agent of the present invention. The form of the antiseptic agent of the present invention can be chosen as appropriate, as long as the effect of compound (I) in the original antiseptic agent of the present invention is not affected.

As described above, the antiseptic agent of the present invention with superior antiseptic effectiveness and superior safety is thus provided.

B. Embodiments of the Endermic Liniment Composition of the Present Invention The endermic liniment composition of the present invention is an endermic liniment composition which contains the antiseptic agent of the present invention as described above.

The blend ratio of the antiseptic agent of the present invention in the endermic liniment composition of the present invention is, for full manifestation of the desired antiseptic effect in the endermic liniment composition, preferably 0.05 wt % or more, more preferably 0.5 wt % or more, in compound (I) equivalent, of the total amount of the composition (hereafter, the blend ratio of the antiseptic agent of the present invention will be expressed in compound (I) equivalent, unless specified otherwise). The antiseptic effect can be significantly increased by blending in 1.0 wt % or more of the total amount of the composition When the blend ratio of the antiseptic agent of the present invention is 1.5 wt % or more, a superior antiseptic effect can be achieved essentially without using antiseptic components other than compound (I) which is an effective component of the antiseptic agent of the present invention such as paraoxy benzoate (commonly called parabens), salcylic acid and sorbic acid or antiseptic assistants such as phenoxy ethanol ["essentially without using other antiseptic components" means either antiseptic components other than compound (I) are not used at all, or the antiseptic effect of the other antiseptic component is latent in the endermic liniment composition (an example is a case when a compound which can be used for the other antiseptic component is used for a purpose unrelated to its antiseptic effect)].

The upper limit of the blend ratio of the antiseptic agent of the present invention in the endermic liniment composition of the present invention should not be limited in particular. However, usually if the blend ratio is more than 3.0 wt % of the total amount of the composition then the skin sensation at the time of use tends to become heavy; and if it is more than 10.0 wt %, then compound (I)'s characteristic odor becomes conspicuous and the quality of the endermic liniment composition tends to be degraded.

Also, diols such as propylene glycol, 1,3-butylene glycol, 1,2-pentane diol, dipropylene glycol, 1,2-butylene glycol, 2,5-hexane diol, 2,4-pentane diol, 2-methyl-2,4-pentane diol, 1,2-hexylene glycol, 1,6-hexylene glycol, and 1,5-pentane diol, of which the most preferable is 1,3-butylene glycol, can be used in combination with compound (I) in the endermic liniment composition of the present invention. In this case, even when the blend ratio of compound (I) in the endermic liniment composition is relatively low, adequate antiseptic properties are surprisingly ensured without adding antiseptic agents such as paraben or antiseptic assistants such as phenoxy ethanol, and an endermic liniment composition superior in both usability and safety is provided. Particularly, the endermic liniment composition of the present invention with this combination of components tends to be superior in usability and thus preferable. When this combination of components is used, the blend ratio of the aforementioned diol in the endermic liniment composition of the present invention is preferably 0.1–15 wt % of the total amount of the composition and 0.1–20 times (weight ratio) the amount of compound (I).

The present invention does not exclude the addition of other antiseptic components and/or antiseptic assistant components to the endermic liniment composition of the present invention as desired, even if compound(I) can provide adequate antiseptic effectiveness to the endermic liniment composition of the present invention and there is no need to add other antiseptic components and/or; antiseptic assistant components.

"2: The Invention of Claims 6 and 7"

(1) 3-methyl-3-methoxybutanol, which is one of the two essential components blended in the endermic liniment composition (hereafter referred to as "the present invention's endermic liniment composition"), has a structure represented by the following formula.

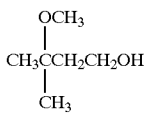

This compound is a component normally blended in an endermic liniment composition as one of the solvents of perfumes. It can be prepared with a common prior art method and blended in the present invention's endermic liniment composition. Commercially available products (such as those from Kuraray Co., Ltd.) can also be blended in the present invention's endermic liniment composition.

The blend ratio of 3-methyl-3-methoxybutanol in the present invention's endermic liniment composition is not limited in particular, and can be determined as appropriate depending on the required degree of antiseptic effectiveness and the blend ratio of 1,2-pentane diol which is used in combination with it. In order to effectively manifest the desired antiseptic effect in the endermic liniment composition, 0.1 wt % or more of the total composition is a preferable blend ratio. The upper limit of the blend ratio is not limited in particular; 10.0 wt % of the total amount of the composition is sufficient and no improvement in the effect can be expected by increasing it further.

(2) 1,2-pentanediol, which is another essential component to be blended in the present invention's endermic liniment composition along with the aforementioned 3-methyl-3-methoxybutanol, is a compound with a structure represented by the following formula.

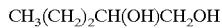

This 1,2-pentanediol is a component normally blended in an endermic liniment composition as one of the humectants. For the 1,2-pentanediol to be blended in the present invention's endermic liniment composition, those prepared with a normal prior method can be used. Commercially available products (such as those from DRAGOCO) can also be used.

The blend ratio of 1,2-pentanediol in the present invention's endermic liniment composition is not limited in particular, and can be determined as appropriate depending on the required degree of antiseptic effectiveness and the blend ratio of 3-methyl-3-methoxybutanol which is used in combination with it. In order to effectively manifest the desired antiseptic effect in the endermic liniment composition, 0.1 wt % or more of the total composition is a preferable blend ratio.

The upper limit of the blend ratio of this 1,2-pentanediol should be decided as appropriate depending on the nature of the endermic liniment composition and should not limited in particular; 10.0 wt % of the total, amount of the composition is sufficient and no improvement in the effect can be expected by increasing it further. Blending 20.0 wt % or more of the total amount of the endermic liniment composition is not preferable because then the usability of the endermic liniment composition is affected due to stickiness and such.

For the relative blend ratio between the aforementioned 3-methyl-3-methoxybutanol and 1,2-pentanediol which are used in the present invention's endermic liniment composition as an antiseptic means, it is preferable if the blend ratio of one is smaller when the blend ratio of the other is larger, or vice versa, for the purpose of effectively manifesting the intended effect of the present invention.

For example, as shown in Examples later, when the blend ratio of 3-methyl-3-methoxybutanol is 0.1 wt % or less (excluding 0 wt %) of the total amount.of the composition, the result is relatively good if 7.0 wt % or more of 1,2-pentanediol is blended in. When the blend ratio of 3-methyl-3-methoxybutanol is more than 0.1 wt % and 2.0 wt % or less of the total amount of the composition, the result is relatively good if 3.0 wt % or more of 1,2-pentanediol is blended in. When the blend ratio of 3-methyl-3-methoxybutanol is more than 2.0 wt % and 4.0 wt % or less of the total amount of the composition, the result is relatively good if 2.0 wt % or more of 1,2-pentanediol is blended in.

When the blend ratio of 3-methyl-3-methoxybutanol is more than 4.0 wt % and 7.0 wt % or less of the total amount of the composition, the result is relatively good if 1.0 wt % or more of 1,2-pentanediol is blended in. When the blend ratio of 3-methyl-3-methoxybutanol is more than 7.0 wt % and 10.0 wt % or less of the total amount of the composition, the result is relatively good if 0.1 wt % or more of 1,2-pentanediol is blended in.

(3) 2-phenoxy ethanol, which is another essential component to be blended in the present invention's endermic liniment composition along with the aforementioned 3-methyl-3-methoxybutanol, is a compound with a structure represented by the following formula. This 2-phenoxy ethanol is a component normally blended in an endermic liniment composition as an antiseptic assitant.

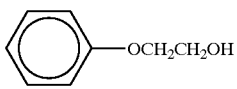

For the 2-phenoxy ethanol to be blended in the present invention's endermic liniment composition, those prepared with a normal prior method, such as a method in which phenol is made to react with ethylene oxide or a method which uses a reaction between sodium phenoxide and ethylene chlorohydrine, can be used. Commercially available products can also be used.

The blend ratio of 2-phenoxy ethanol in the present invention's endermic liniment composition is not limited in particular, and can be determined as appropriate depending on the required degree of antiseptic effectiveness and the blend ratio of 3-methyl-3-methoxybutanol which is used in combination with it. In order to effectively manifest the desired antiseptic effect in the endermic liniment composition, 0.01 wt % or more of the total composition is a preferable blend ratio.

The upper limit of the blend ratio of this 2-phenoxy ethanol should be decided as appropriate depending on the nature of the endermic liniment composition and should not limited in particular. One of the features of the present invention is that the blend ratio of 2-phenoxy ethanol can be reduced. Therefore, the blend ratio of 2-phenoxy ethanol is preferably small in consideration for some users who are sensitive to phenoxy ethanol, as long as the intended effect of the present invention is not affected.

For the relative blend ratio between the aforementioned 3-methyl-3-methoxybutanol and 2-phenoxy ethanol which are used in the present invention's endermic liniment composition as an antiseptic means, it is preferable if the blend ratio of one is smaller when the blend ratio of the other is larger, or vice versa, for the purpose of effectively manifesting the intended effect of the present invention.

For example, as shown in Examples later, when the blend ratio of 3-methyl-3-methoxybutanol is 0.1 wt % or less (excluding 0 wt %) of the total amount of the composition, the result is relatively good if 0.5 wt % or more of 2-phenoxy ethanol is blended in. When the blend ratio of 3-methyl-3-methoxybutanol is more than 0.1 wt % and 1.0 wt % or less of the total amount of the composition, the result is relatively good if 0.3 wt % or more of 2-phenoxy ethanol is blended in. When the blend ratio of 3-methyl-3-methoxybutanol is more than 1.0 wt % and 3.0 wt %. or less, the result is relatively good if 0.1 wt % or more of 2-phenoxy ethanol is blended in.

When the blend ratio of 3-methyl-3-methoxybutanol is more than 3.0 wt % and 5.0 wt % or less of the total amount of the composition, the result is relatively good if 0.05 wt % or more of 2-phenoxy ethanol is blended in. When the blend ratio of 3-methyl-3-methoxybutanol is more than 5.0 wt % and 10.0 wt % or less of the total amount of the composition, the result is relatively good if 0.01 wt % or more of 2-phenoxy ethanol is blended in.

(4) As described above, according to the present invention, by using a new combination of 3-methyl-3-methoxybutanol and 1,2-pentanediol or 2-phenoxy ethanol, an endermic liniment composition can be provided which ensures adequate antiseptic properties and has both superior usability and safety, to our surprise, by using a small amount of 2-phenoxy ethanol without additionally blending in antiseptic agents such as parabens.

"3: Common Description"

Depending on the specific embodiment of the endermic liniment composition, components normally blended in an endermic liniment composition can be blended into the endermic liniment composition of the present invention within the range which does not affect the expected effect of the present invention; such components include humectants, ultraviolet light absorbents, vitamins, animal/plant extracts, anti-inflammatories, whiteners, vasodilators, astringents, refreshers, and hormones.

As described above, the endermic liniment composition of the present invention can be used widely in product forms for application on skin such as cosmetics, drugs, and quasi drugs, and also a wide variety of formulations are possible, such as the aqueous solution system, solubilized system, emulsion system, oil-liquid system, gel system, paste system, ointment system, aerozol system, water-oil two layer system, water-oil-powder three layer system. That is, in terms of basic cosmetics, it can be used widely in the various formulations as described above and in forms such as a cleansing cosmetic, lotion, emulsion, cream, gel, essence, and pack/mask. In terms of hair cosmetics, it can be used widely in the various formulations as described above and in forms such as a shampoo, rinse, hair dressing, and hair restoration cosmetics.

In terms of drugs and quasi drugs, it can be widely used in the forms of various types of ointment, for example. Potential formulations and forms of the endermic liniment composition of the present invention are not limited to these formulations and forms.

Depending on the aforementioned desired formulations and forms, usual prior art base components can be widely blended in the endermic liniment composition of the present invention, as long as the expected effect of the present invention is not affected by this blending. That is, appropriate amounts of liquid fats/oils, solid fats/oils, waxes, hydrocarbon oils, higher fatty acids, higher alcohols, synthetic ester oils, silicones, various surfactants, sequestering agents, water soluble polymers, thickeners, various powder components, colorings, perfumes, and water can be blended as required into the endermic liniment composition of the present invention.

Specific recipes of the endermic liniment composition of the present invention are described below in the Examples section.

EXAMPLES

The present invention is described in detail by referring to the examples below. The technical scope of the present invention is not limited to these examples.

The blend ratios indicated by "wt %" or "%" in the examples are in weight percent units of the total amount of that into which the components were blended, unless specified otherwise.

Before disclosing the examples, the actual usage test and the antiseptic effectiveness evaluation test are described.

The Actual Usage Test

A panel of 30 people who had complained about skin irritation when using endermic liniment compositions containing paraben used the endermic liniment compositions of the present invention and others twice a day, morning and evening, for one week, and reported the degree of satisfaction in terms of usability and presence/absence of skin irritation.

The Antiseptic Effectiveness Evaluation Test 30 ml of the sample was inoculated with microbe-containing fluid, and the change in the number of microbes was checked with the smearing method. Mold, yeast, and bacteria were used as the inoculation microbes. The antiseptic effectiveness was evaluated based on the changes in the number of the microbes in two weeks, and the obtained results were classified by using the following four step criterion. Of the following classes, ⊚ and ○ were defined as acceptable.

⊚: A rapid reduction in microbes was observed for all the microbe types.

○: A gradual reduction in microbes was observed for all the microbe types.

Δ: No reduction in microbes was observed for some microbes.

X: No reduction in microbes was observed.

1: "Examples of Claims 1–5"

Examples 1-1–1-4 and Comparative Example 1-1

Using the recipes shown in the following Table 1-1, lotions which were embodiments of the endermic liniment composition of the present invention as well as comparative examples were subjected to the aforementioned actual usage test and antiseptic effectiveness, evaluation test, and the results were recorded. For the preparation method of these lotions, a method commonly used for preparing lotions was used.

TABLE 1-1

(Blend ratio: wt %)

|  | Example 1-1 | Example 1-2 | Example 1-3 | Example 1-4 | Comparative example 1-1 |
|---|---|---|---|---|---|
| 2-n-butyl-2-ethyl-1,3-propanediol | 0.5 | 1.0 | 1.0 | 0.5 | — |
| 1,3-butylene glycol | 2.0 | 2.0 | — | — | 2.0 |
| Ethyl alcohol | 3.0 | 3.0 | 3.0 | 3.0 | 3.0 |
| Glycerine | 1.0 | 1.0 | 1.0 | 1.0 | 1.0 |
| Polyoxyethylene (POE = 60) hydrogenated castor oil | 0.4 | 0.4 | 0.4 | 0.4 | 0.4 |
| Citric acid | 0.03 | 0.03 | 0.03 | 0.03 | 0.03 |
| Trisodium citrate | 0.07 | 0.07 | 0.07 | 0.07 | 0.07 |
| Trisodium edetate | 0.02 | 0.02 | 0.02 | 0.02 | 0.02 |
| Methyl paraben | — | — | — | 0.2 | — |
| Purified water | Balance to make the total 100 | | | | |
| <Results of the actual usage test> | | | | | |
| Those who complained about skin irritation | 0/30 | 0/30 | 0/30 | 14/30 | 0/30 |
| Those who were satisfied with the usability | 29/30 | 29/30 | 28/30 | 26/30 | 28/30 |
| Results of the antiseptic effectiveness test | ○ | ◎ | ◎ | ◎ | X |

With Examples 1-1 and 1-2, the majority of people in the panel reported that skin irritation was minor and usability was satisfactory, and these Examples also showed superior antiseptic effectiveness.

Even with Example 1-3 which didn't contain 1,3-butylene glycol, the majority of people in the panel reported that skin irritation was minor and usability was satisfactory, and there was no problem in terms of antiseptic effectiveness. On the other hand, with Comparative example 1-1 which did not contain 2-n-butyl-2-ethyl-1,3-propanediol, although the majority of people in the panel reported that skin irritation was minor and usability was satisfactory, the antiseptic effectiveness was inferior.

With Example 1-4 which contained methyl paraben, although the antiseptic effectiveness was superior, many panelists reported skin irritation such as itching and tingling.

These results clearly indicate that an endermic liniment composition which maintains the antiseptic effectiveness, causes less skin irritation, and has good usability is provided by blending the antiseptic agent of the present invention into the endermic liniment composition such that the blend ratio of 2,2-dialkyl-1,3-ptopanediol is approximately 0.5–1%, even when paraben is not blended in.

Examples 1-5–1-15

Using lotions with various blend ratios of 2-n-butyl-2-ethyl-1,3-propanediol, the aforementioned antiseptic effectiveness test and the actual usage test (only usability) were conducted.

The blend ratio of 2-n-butyl-2-ethyl-1,3-propanediol in each lotion and the test results are shown in Table 1-2.

TABLE 1-2

(Blend ratio: wt %)

| | Example | | | | | | | | | | |
|---|---|---|---|---|---|---|---|---|---|---|---|
| | 1-5 | 1-6 | 1-7 | 1-8 | 1-9 | 1-10 | 1-11 | 1-12 | 1-13 | 1-14 | 1-15 |
| 2-n-butyl-2-ethyl-1,3-propanediol | 0.05 | 0.1 | 0.5 | 1.0 | 2.0 | 3.0 | 5.0 | 10.0 | 0.6 | 2.0 | 10.0 |
| 1,3-butylene glycol | 5.0 | 5.0 | 5.0 | 4.0 | 4.0 | 4.0 | 4.0 | 0.2 | — | — | — |
| <Results of the actual usage test> | | | | | | | | | | | |
| Those who were satisfied with the usability | 29/30 | 28/30 | 28/30 | 29/30 | 23/30 | 16/30 | 10/30 | 2/30 | 27/30 | 15/30 | 0/30 |
| Results of the antiseptic effectiveness test | Δ | ○ | ○ | ◎ | ◎ | ◎ | ◎ | ◎ | Δ | ◎ | ◎ |

Table 1-2 indicates that the endermic liniment compositions of the present invention showed adequate antiseptic effectiveness when they contained the antiseptic agent of the present invention such that the concentration of 2-n-butyl-2-ethyl-1,3-propanediol was 0.5% or more. Even at 0.1%, however, an adequate effect on bacteria was confirmed if 1,3-butylene glycol was additionally blended into the endermic liniment composition. The comprehensive evaluation confirmed that 0.5% or more was desirable to have an effect on all the mold, yeast, and bacteria. However, for products with a lower water content of 40–60%, such as nourishing cream, even a blend ratio of 0.3% is expected to have an adequate effect because the concentration of 2-n-butyl-2-ethyl-1,3-propanediol in the water phase increases. On the other hand, when the blend ratio of the antiseptic agent of the present invention in the endermic liniment composition became 3% or more in 2-n-butyl-2-ethyl-1,3-propanediol equivalent, although there was no problem in terms of the antiseptic effect, the usability became heavy and the panel's response became negative.

These results confirmed that by blending in a small amount, in 2-n-butyl-2-ethyl-1,3-propanediol equivalent, of the antiseptic agent of the present invention, an endermic liniment composition with superior antiseptic effectiveness and good skin sensation during use can be provided without blending in antiseptic agents such as paraben or by reducing the amount of antiseptic agents.

Those which did not contain 1,3-butylene glycol (Examples 1-13–1-15) showed superior antiseptic effectiveness by blending in the antiseptic agent of the present invention, but their usability clearly decreased when the amount of the antiseptic agent of the present invention was increased to further improve the antiseptic effectiveness. On the other hand, when 1,3-butylene glycol was added in combination, not only did this addition contribute to the antiseptic effectiveness but the usability was also improved.

Examples of endermic liniment compositions of the present invention with various recipes are shown below. All Examples had less skin irritation and good usability while maintaining superior antiseptic effectiveness. For the method of preparing endermic liniment compositions of these Examples, commonly used methods for preparing endermic liniment compositions of each embodiment were followed. The amount of water was adjusted such that the total amount would be 100.

Example 1-16
Astringent Lotion
Component in the composition blend ratio (wt %)

| | |
|---|---|
| 2-n-butyl-2-ethyl-1,3-propanediol | 1.0 |
| Polyoxyethylene (POE = 50) oleyl ether | 0.5 |
| Polyethylene glycol 300 | 1.0 |
| Ethyl alcohol | 8.0 |
| Glycerine | 3.0 |
| Lactic acid | 0.02 |
| 50% aqueous solution of sodium lactate | 0.25 |
| Trisodium edetate | 0.1 |
| Purified water | Balance |

Example 1-17
Astringent Lotion
Component in the composition blend ratio (wt %)

| | |
|---|---|
| 2,2-diethyl-1,3-propanediol | 1.0 |
| Polyoxyethylene (POE = 50) oleyl ether | 0.5 |
| Polyethylene glycol 300 | 1.0 |
| Ethyl alcohol | 8.0 |
| Glycerine | 3.0 |
| Lactic acid | 0.02 |
| 50% aqueous solution of sodium lactate | 0.25 |
| Trisodium edetate | 0.1 |
| Purified water | Balance |

Example 1-18
Cleansing Foam
Component in the composition blend ratio (wt %)

| | |
|---|---|
| Stearic acid | 8.0 |
| Palmitic acid | 6.0 |
| Myristic acid | 6.0 |
| Lauric acid | 4.0 |
| Potassium hydroxide | 5.2 |
| Glyceryl monostearate | 2.0 |
| Beeswax | 1.5 |
| 2,2-di-n-butyl-1,3-propanediol | 0.6 |
| 1,2-pentanediol | 1.0 |
| Polyethylene glycol 1500 | 5.0 |
| Glycerine | 10.0 |
| Purified water | Balance |

Example 1-19
Emollient Emulsion
Component in the composition blend ratio (wt %)

| | |
|---|---|
| 2-n-propyl-2-n-butyl-1,3-propanediol | 0.1 |
| Glycerine | 5.0 |
| Cetanol | 1.5 |
| Stearyl alcohol | 1.8 |
| Petrolatum | 2.0 |
| Dimethylpolysiloxane (20 cs) | 1.5 |
| Squalane | 2.5 |
| Isopropyl myristate | 2.5 |
| Glyceryl monostearate | 1.8 |
| Polyoxyethylene (POE = 5) glyceryl monostearate | 1.8 |
| Polyoxyethylene (POE = 20) cetyl ether | 1.5 |
| Carboxyvinyl polymer | 0.25 |
| Potassium hydroxide | 0.05 |
| L-arginine | 0.2 |
| Xylitol | 2.0 |
| Dipropylene glycol | 2.0 |
| 1,3-butylene glycol | 3.0 |
| Trisodium edetate | 0.02 |
| Purified water | Balance |

Example 1-20
Skin Treatment Gel
Component in the composition blend ratio (wt %)

| | |
|---|---|
| 2,2-di-n-propyl-1,3-propanediol | 1.0 |
| Dimethylpolysiloxane | 0.5 |
| Isopropyl myristate | 1.5 |
| Polyoxyethylene (POE = 60) hydrogenated castor oil | 0.5 |
| Tocopherol acetate | 0.2 |
| Monoammonium glycyrrhizate | 0.05 |
| Carboxyvinyl polymer | 0.45 |
| Potassium hydroxide | 0.15 |
| Glycerine | 12.0 |
| Dipropylene glycol | 2.0 |
| Trisodium edetate | 0.01 |
| Purified water | Balance |

Example 1-21
Moisture Cream
Component in the composition blend ratio (wt %)

| | |
|---|---|
| 2-n-propyl-2-isopropyl-1,3-propanediol | 1.0 |
| Stearyl alcohol | 5.5 |
| Stearic acid | 2.0 |
| Squalane | 12.5 |
| Isopropyl myristate | 7.5 |
| Polyoxyethylene (POE = 25) cetyl alcohol ether | 3.0 |
| Glyceryl monostearate | 2.0 |
| Tocopherol acetate | 0.2 |

Example 1-22
Essence
Component in the composition blend ratio (wt %)

| | |
|---|---|
| 2-isopropyl-2-ethyl-1,3-propanediol | 1.0 |
| Dimethylpolysiloxane | 0.1 |
| Olive oil | 0.2 |
| Polyoxyethyleneoleyl alcohol ether | 1.0 |
| Tocopherol acetate | 0.1 |
| Ethanol | 6.5 |
| Hyaluronic acid | 0.1 |
| Sorbitol | 8.0 |
| Dipropylene glycol | 2.0 |
| Trisodium edetate | 0.01 |
| Purified water | Balance |

Example 1-23
Essence
Component in the composition blend ratio (wt %)

| | |
|---|---|
| 2-n-propyl-2-ethyl-1,3-propanediol | 1.0 |
| Dimethylpolysiloxane | 0.1 |
| Olive oil | 0.2 |
| Polyoxyethyleneoleyl alcohol ether | 1.0 |
| Tocopherol acetate | 0.1 |
| Ethanol | 6.5 |
| Hyaluronic acid | 0.1 |
| Sorbitol | 8.0 |
| Dipropylene glycol | 2.0 |
| Trisodium edetate | 0.01 |
| Purified water | Balance |

Example 1-24
Jelly Pack
Component in the composition blend ratio (wt %)

| | |
|---|---|
| 2,2-diisopropyl-1,3-propanediol | 1.0 |
| Polyoxyethyleneoleyl alcohol ether | 0.5 |
| Monoammonium glycyrrhizate | 0.05 |
| Carboxymethyl cellulose | 5.0 |
| Ethanol | 12.0 |
| Polyvinyl alcohol | 12.0 |
| 1,3-butylene glycol | 5.0 |
| Trisodium edetate | 0.01 |
| Purified water | Balance |

Example 1-25
Eye Liner
Component in the composition blend ratio (wt %)

| | |
|---|---|
| 2-isopropyl-2-n-butyl-1,3-propanediol | 0.6 |
| Iron oxide (black) | 14.0 |
| Isopropyl myristate | 1.5 |
| Polyoxyethylenesorbitan monooleate | 1.0 |
| Vinyl acetate resin emulsion | 45.0 |
| Monoammonium glycyrrhizate | 0.05 |
| Carboxyvinyl polymer | 1.5 |
| Acetyltributyl citrate | 1.0 |
| Glycerine | 5.0 |
| Dipropylene glycol | 2.0 |
| Trisodium edetate | 0.01 |
| Purified water | Balance |

2: "Examples of Claim 6"

Examples 2-1, 2-2 and Comparative Examples 2-1–2-31

Using the recipes shown in the following Table 2-1, lotions of Examples 2-1 and 2-2, as an embodiment of the present invention's endermic liniment composition, and lotions of Comparative examples 2-1, 2-2, and 2-3 were subjected to the aforementioned test of usability and such and antiseptic effectiveness evaluation test, and the results are listed in Table 2-1 as well. For the preparation method of these lotions, a method commonly used for preparing lotions was used.

TABLE 2-1

(Blend ratio: wt %)

| | Example | | Comparative example | | |
|---|---|---|---|---|---|
| | 2-1 | 2-2 | 2-1 | 2-2 | 2-3 |
| 3-methyl-3-methoxybutanol | 1.0 | 3.0 | 3.0 | — | 3.0 |
| 1,2-pentanediol | 3.0 | 3.0 | — | 3.0 | 3.0 |
| Ethyl alcohol | 2.0 | 2.0 | 2.0 | 2.0 | 2.0 |
| Glycerine | 1.0 | 1.0 | 1.0 | 1.0 | 1.0 |
| Polyoxyethylene (POE = 60) hydrogenated castor oil | 0.4 | 0.4 | 0.4 | 0.4 | 0.4 |
| Citric acid | 0.03 | 0.03 | 0.03 | 0.03 | 0.03 |
| Trisodium citrate | 0.07 | 0.07 | 0.07 | 0.07 | 0.07 |
| Trisodium edetate | 0.02 | 0.02 | 0.02 | 0.02 | 0.02 |
| Methyl paraben | — | — | — | — | 0.2 |
| Purified water | Balance to make the total 100 | | | | |
| <Results of the actual usage test> | | | | | |
| Those who complained about skip irritation | 0/30 | 0/30 | 0/30 | 0/30 | 21/30 |
| Those who were satisfied with the usability | 29/30 | 28/30 | 28/30 | 29/30 | 26/30 |
| Antiseptic effectiveness test | ◯ | ◉ | X | X | ◉ |

As indicated in the results shown in Table 2-1, with Examples 1 and 2, the majority of people in the panel reported that skin irritation was minor and usability was satisfactory, and these Examples also showed superior antiseptic effectiveness. On the other hand, with Comparative example 2-1 which did not contain 1,2-pentanediol, although the majority of people in the panel reported that skin irritation was minor and usability was satisfactory, the antiseptic effectiveness was inferior. Also, with Comparative example 2-2 which did not contain 3-methyl-3-methoxybutanol, although the majority of people in the panel reported that skin irritation was minor and usability was satisfactory, the antiseptic effectiveness was inferior. With Comparative example 2-3 which contained methyl paraben, although the antiseptic effectiveness was superior, many panelists reported skin irritation. These results clearly indicate that the combination of 3-methyl-3-methoxybutanol and 1,2-pentanediol can provide an endermic liniment composition which shows less skin irritation and good usability while maintaining the antiseptic effectiveness.

Examples 2-3–2-8 and Comparative Examples 2-4 and 2-5

Following these Examples and Comparative examples, the aforementioned antiseptic effectiveness test and the usability test were conducted on lotions with varied blend ratios of 3-methyl-3-methoxybutanol and 1,2-pentanediol (the components and their blend ratios other than 3-methyl-3-methoxybutanol and 1,2-pentanediol are the same as those shown in the aforementioned Table 2-1). The blend ratios of 3-methyl-3-methoxybutanol and 1,2-pentanediol in each lotion and the test results are shown in Table 2-2.

TABLE 2-2

(Blend ratio: wt %)

| | Examples | | | | | | Comparative examples | |
|---|---|---|---|---|---|---|---|---|
| | 2-3 | 2-4 | 2-5 | 2-6 | 2-7 | 2-8 | 2-4 | 2-5 |
| 3-methyl-3-methoxy-butanol | 0.1 | 2.0 | 4.0 | 7.0 | 10.0 | 10.0 | 4.0 | 10.0 |
| 1,2-pentanediol | 7.0 | 3.0 | 2.0 | 1.0 | 0.1 | 0.5 | — | — |
| <Usability test results> | | | | | | | | |
| those who are satisfied with usability | 28/30 | 29/30 | 30/30 | 28/30 | 30/30 | 29/30 | 29/30 | 29/30 |
| Antiseptic effectiveness | ○ | ○ | ○ | ○ | ○ | ⊙ | X | Δ |

According to the test results shown in Table 2-2, Example 2-3, which had 0.1 wt % of 3-methyl-3-methoxybutanol, showed satisfactory results with 7.0 wt % of 1,2-pentanediol. Example 2-4, which had 2.0 wt % of 3-methyl-3-methoxybutanol, showed satisfactory results with 3.0 wt % of 1,2-pentanediol. Example 2-5, which had 4.0 wt % of 3-methyl-3-methoxybutanol, showed satisfactory results with 2.0 wt % of 1,2-pentanediol.

Also, Example 2-6, which had 7.0 wt % of 3-methyl-3-methoxybutanol, showed satisfactory results with 1.0 wt % of. 1,2-pentanediol. Examples 2-7 and 2-8, which had 10 wt % of 3-methyl-3-methoxybutanol, showed satisfactory results in terms of both usability and antiseptic effectiveness with 0.1 wt % (Example 2-7) and 0.5 wt % (Example 2-8) of 1,2-pentanediol. Example 2-8, which had a higher blend ratio of 1,2-pentanediol, showed particularly superior antiseptic effectiveness.

Comparative examples 2-4 and 2-5, which did not contain any 1,2-pentanediol, both showed inadequate antiseptic effectiveness. These test results also clearly indicated that not only the amount of 3-methyl-3-methoxybutanol and the amount of 1,2-pentanediol blended in the endermic liniment composition of the present invention but also their relative blend ratio influences the intended effect of the present invention.

In terms of the blend ratios of 3-methyl-3-methoxybutanol and 1,2-pentanediol in the present invention's endermic liniment composition, these results clearly indicate that, when the blend ratio of 3-methyl-3-methoxybutanol is 0.1 wt % or less (excluding 0 wt %), the result is relatively good if 7.0 wt % or more of 1,2-pentanediol is blended in. It was also indicated that, when the blend ratio of 3-methyl-3-methoxybutanol is more than 0.1 wt % and 2.0 wt % or less, the result is relatively good if 3.0 wt % or more of 1,2-pentanediol is blended in.

It was also indicated that, when the blend ratio of 3-methyl-3-methoxybutanol is more than 2.0 wt % and 4.0 wt % or less, the result is relatively good if 2 wt % or more of 1,2-pentanediol is blended in. It was also indicated that, when the blend ratio of 3-methyl-3-methoxybutanol is more than 4.0 wt % and 7.0 wt % or less, the result is relatively good if 1.0 wt % or more of 1,2-pentanediol is blended in. Furthermore, it was indicated that, when the blend ratio of 3-methyl-3-methoxybutanol is more than 7.0 wt % and 10.0 wt % or less, the result is relatively good if 0.1 wt % or more of 1,2-pentanediol is blended in.

Examples of endermic liniment compositions of the present invention with various recipes are shown below. All Examples had less skin irritation and good usability while maintaining superior antiseptic effectiveness. For the method of preparing endermic liniment compositions of these Examples, commonly used methods for preparing endermic liniment compositions of each embodiment were followed.

Example 2-9

Astringent Lotion

| | wt % |
|---|---|
| 3-methyl-3-methoxybutanol | 1.0 |
| 1,2-pentanediol | 3.0 |
| Polyoxyethylene (POE = 50) oleyl ether | 0.5 |
| Polyethylene glycol 300 | 1.0 |
| Ethyl alcohol | 8.0 |
| Dipropylene glycol | 2.0 |
| Lactic acid | 0.02 |
| 50% aqueous solution of sodium lactate | 0.25 |
| Trisodium edetate | 0.01 |
| Purified water | Balance |

Example 2-10

Emollient Emulsion

| | wt % |
|---|---|
| 3-methyl-3-methoxybutanol | 0.1 |
| 1,2-pentanediol | 5.0 |
| Cetanol | 1.5 |
| Stearyl alcohol | 1.8 |
| Petrolatum | 2.0 |
| Dimethylpolysiloxane (20 cs) | 1.5 |
| Squalane | 2.5 |
| Isopropyl myristate | 2.5 |
| Glyceryl monostearate | 1.8 |
| Polyoxyethylene (POE = 5) glyceryl monostearate | 1.8 |
| Polyoxyethylene (POE = 20) cetyl ether | 1.5 |
| Carboxyvinyl polymer | 0.25 |
| Potassium hydroxide | 0.05 |
| L-arginine | 0.2 |
| Glycerine | 4.0 |
| Dipropylene glycol | 1.0 |
| 1,3-butylene glycol | 2.0 |
| Trisodium edetate | 0.02 |
| Purified water | Balance |

Example 2-11

Skin Treatment Gel

|  | wt % |
|---|---|
| 3-methyl-3-methoxybutanol | 1.0 |
| 1,2-pentanediol | 3.0 |
| Dimethylpolysiloxane | 0.5 |
| Isopropyl myristate | 1.5 |
| Polyoxyethylene (POE = 60) hydrogenated castor oil | 0.5 |
| Tocopherol acetate | 0.2 |
| Monoammonium glycyrrhizate | 0.05 |
| Carboxyvinyl polymer | 0.45 |
| Potassium hydroxide | 0.15 |
| Glycerine | 16.0 |
| Dipropylene glycol | 2.0 |
| Trisodium edetate | 0.01 |
| Purified water | Balance |

3: "Examples of Claim 7"

Examples 3-1, 2 and Comparative Examples 3-1, 3-2

Using the recipes shown in the following Table 3-1, lotions of Examples 3-1 and 3-2, as an embodiment of the present invention's endermic liniment composition, and lotions of Comparative examples 3-1 and 3-2 were subjected to the aforementioned test of usability and such and antiseptic effectiveness evaluation test, and the results are listed in Table 3-1 as well. For the preparation method of these lotions, a method commonly used for preparing lotions was used.

TABLE 3-1

(Blend ratio: wt %)

|  | Example | | Comparative Example | |
|---|---|---|---|---|
|  | 3-1 | 3-2 | 3-1 | 3-2 |
| 3-methyl-3-methoxybutanol | 3.0 | 5.0 | 3.0 | 3.0 |
| 2-phenoxy ethanol | 0.5 | 0.5 | — | — |
| Ethyl alcohol | 2.0 | 2.0 | 2.0 | 2.0 |
| Glycerine | 1.0 | 1.0 | 1.0 | 1.0 |
| Polyoxyethylene (POE = 60) hydrogenated castor oil | 0.4 | 0.4 | 0.4 | 0.4 |
| Citric acid | 0.03 | 0.03 | 0.03 | 0.03 |
| Trisodium citrate | 0.07 | 0.07 | 0.07 | 0.07 |
| Trisodium edetate | 0.02 | 0.02 | 0.02 | 0.02 |
| Methyl paraben | — | — | — | 0.2 |
| Purified water | Balance to make the total 100 | | | |
| <Results of the usability test> | | | | |
| Those who complained about skin irritation | 0/30 | 0/30 | 0/30 | 21/30 |
| Those who were satisfied with the usability | 29/30 | 28/30 | 28/30 | 26/30 |
| Results of the antiseptic effectiveness test | ◯ | ◉ | x | ◉ |

As indicated in the results shown in Table 3-1, with Examples 3-1 and 3-2, the majority of people in the panel reported that skin irritation was minor and usability was satisfactory, and these Examples also showed superior antiseptic effectiveness. On the other hand, with Comparative example 3-1 which did not contain 2-phenoxy ethanol, although the majority of people in the panel reported that skin irritation was minor and usability was satisfactory, the antiseptic effectiveness was inferior when the blend ratio of 3-methyl-3-methoxybutanol was low.

With Comparative example 3-2 which contained methyl paraben but did not contain 2-phenoxy ethanol just as Comparative example 3-1 did not, although the antiseptic effectiveness was superior, many panelists reported skin irritation. These results clearly indicate that the combination of 3-methyl-3-methoxybutanol and 2-phenoxy ethanol can provide an endermic liniment composition which shows less skin irritation and good usability while maintaining the antiseptic effectiveness.

Examples 3-3–3-7 and Comparative Examples 3-3 and 3-4

Next, the aforementioned antiseptic effectiveness test an.d the usability test were conducted on lotions witch varied blend ratios of 3-methyl-3-methoxybutanol and 2-phenoxy ethanol (the components and their blend ratios other than 3-methyl-3-methoxybutanol and 2-phenoxy ethanol are the same as those shown in the aforementioned Table 3-1). The blend ratios of 3-methyl-3-methoxybutanol and 2-phenoxy ethanol in each lotion and the test results are shown in Table 3-2.

TABLE 3-2

(Blend ratio: wt %)

|  | Examples | | | | | Comparative examples | |
|---|---|---|---|---|---|---|---|
|  | 3-3 | 3-4 | 3-5 | 3-6 | 3-7 | 3-4 | 3-5 |
| 3-methyl-3-methoxybutanol | 0.1 | 1.0 | 3.0 | 5.0 | 10.0 | 3.0 | 10.0 |
| 2-phenoxy ethanol | 0.5 | 0.3 | 0.1 | 0.05 | 0.01 | — | — |
| <Results of the usability test> | | | | | | | |
| Those who were satisfied with the usability | 29/30 | 28/30 | 29/30 | 28/30 | 27/30 | 27/30 | 26/30 |
| Results of the antiseptic effectiveness test | ◯ | ◯ | ◯ | ◯ | ◯ | X | X |

According to the test results shown in Table 3-2, Example 3-3, which had 0.1 wt % of 3-methyl-3-methoxybutanol, showed satisfactory results with 0.5 wt % of 2-phenoxy ethanol. Example 3-4, which had 1.0 wt % of 3-methyl-3-methoxybutanol, showed satisfactory results with 0.3 wt % of 2-phenoxy ethanol. Example 3-5, which had 3.0 wt % of 3-methyl-3-methoxybutanol, showed satisfactory results with 0.1 wt % of 2-phenoxy ethanol.

Also, Example 3-6, which had 5.0 wt % of 3-methyl-3-methoxybutanol, showed satisfactory results with 0.05 wt % of 2-phenoxy ethanol. Examples 3-7, which had 10 wt % of 3-methyl-3-methoxybutanol, showed satisfactory results in terms of both usability and antiseptic effectiveness with 0.01 wt % of 2-phenoxy ethanol. Comparative examples 3-4 and 3-5, which did not contain any 2-phenoxy ethanol, both showed inadequate antiseptic effectiveness.

In terms of the blend ratios of 3-methyl-3-methoxybutanol and 2-phenoxy ethanol in the present invention's endermic liniment composition, these results clearly indicate that, when the blend ratio of 3-methyl-3-methoxybutanol is 0.1 wt % or less (excluding 0 wt %), the result is relatively good if 0.5 wt % or more of 2-phenoxy ethanol is blended in. It was also indicated that, when the blend ratio of 3-methyl-3-methoxybutanol is more than 0.1 wt % and 1.0 wt % or less, the result is relatively good if 0.3 wt % or more of 2-phenoxy ethanol is blended in.

It was also indicated that, when the blend ratio of 3-methyl-3-methoxybutanol is more than 1.0 wt % and 3.0 wt % or less, the result is relatively good if 0.1 wt % or more of 2-phenoxy ethanol is blended in. It was also indicated that, when the blend ratio of 3-methyl-3-methoxybutanol is more than 3.0 wt % and 5.0 wt % or less, the result is relatively good if 0.05 wt % or more of 2-phenoxy ethanol is blended in. Furthermore, it was indicated that, when the blend ratio of 3-methyl-3-methoxybutanol is more than 5.0 wt % and 10.0 wt % or less, the result is relatively good if 0.01 wt % or more of 2-phenoxy ethanol is blended in.

Examples of endermic liniment compositions of the present invention with various recipes are shown below. All Examples had less skin irritation and good usability while maintaining superior antiseptic effectiveness. For the method of preparing endermic liniment compositions of these Examples, commonly used methods for: preparing endermic liniment compositions of each embodiment were followed.

Example 3-8
Astringent Lotion

|  | wt % |
|---|---|
| 3-methyl-3-methoxybutanol | 1.0 |
| 2-phenoxy ethanol | 0.3 |
| Polyoxyethylene (POE = 50) oleyl ether | 0.5 |
| Polyethylene glycol 300 | 1.0 |
| Ethyl alcohol | 18.0 |
| Dipropylene glycol | 2.0 |
| Lactic acid | 0.02 |
| 50% aqueous solution of sodium lactate | 0.25 |
| Trisodium edetate | 0.01 |
| Purified water | Balance |

Example 3-9
Emollient Emulsion

|  | wt % |
|---|---|
| 3-methyl-3-methoxybutanol | 5.0 |
| 2-phenoxy ethanol | 0.1 |
| Cetanol | 1.5 |
| Stearyl alcohol | 1.8 |
| Petrolatum | 2.0 |
| Dimethylpolysiloxane (20 cs) | 1.5 |
| Squalane | 2.5 |
| Isopropyl myristate | 2.5 |
| Glyceryl monostearate | 1.8 |
| Polyoxyethylene (POE = 5) glyceryl monostearate | 1.8 |
| Polyoxyethylene (POE = 20) cetyl ether | 1.5 |
| Carboxyvinyl polymer | 0.25 |
| Potassium hydroxide | 0.05 |
| L-arginine | 0.2 |
| Glycerine | 4.0 |
| Dipropylene glycol | 2.0 |
| 1,3-butylene glycol | 3.0 |

-continued

|  | wt % |
|---|---|
| Trisodium edetate | 0.02 |
| Purified water | Balance |

Example 3-10
Skin Treatment Gel

|  | wt % |
|---|---|
| 3-methyl-3-methoxybutanol | 3.0 |
| 2-phenoxy ethanol | 0.3 |
| Dimethylpolysiloxane | 0.5 |
| Isopropyl myristate | 1.5 |
| Polyoxyethylene (POE = 60) hydrogenated castor oil | 0.5 |
| Tocopherol acetate | 0.2 |
| Monoammonium glycyrrhizate | 0.05 |
| Carboxyvinyl polymer | 0.45 |
| Potassium hydroxide | 0.15 |
| Glycerine | 16.0 |
| Dipropylene glycol | 2.0 |
| Trisodium edetate | 0.01 |
| Purified water | Balance |

What is claimed is:

1. A method of treating the skin with an antiseptic/antifungal composition comprising applying to the skin an endermic liniment composition which contains 1–3 wt. % of 3-methyl-3-methoxybutanol and greater than 0 and no more than 3 wt. % of 1,2-pentanediol as an antimicrobial/antibacterial agent.

2. A method of preserving a cosmetic with an antiseptic/antifungal composition comprising mixing a substantially paraben-free antiseptic/antifungal composition which contains 3-methyl-3-methoxybutanol and 1,2-pentanediol in cosmetic form into said cosmetic.

3. The method of claim 2, wherein the 3-methyl-3-methoxybutanol is greater than 0.1 wt % of the total composition and equal to or smaller than 2.0 wt % of the total composition, and the 1,2-pentanediol is equal to or greater than 3.0 wt % of the total composition.

4. A substantially paraben-free antiseptic/antifungal composition which contains 3-methyl-3-methoxybutanol and 2-phenoxy ethanol in cosmetic form.

5. A method of treating the skin with an antiseptic/antifungal composition comprising applying to the skin an antiseptic/antifungal composition comprising 3-methyl-3-methoxybutanol and 2-phenoxy ethanol in cosmetic form.

* * * * *